United States Patent [19]
Schwartzman

[11] Patent Number: 5,755,661
[45] Date of Patent: May 26, 1998

[54] PLANAR ABDOMINAL WALL RETRACTOR FOR LAPAROSCOPIC SURGERY

[76] Inventor: Alexander Schwartzman, 350 Henry St., Brooklyn, N.Y. 11201

[21] Appl. No.: 376,350

[22] Filed: Jan. 23, 1995

Related U.S. Application Data

[63] Continuation-in-part of Ser. No. 78,576, Jun. 17, 1993, abandoned.

[51] Int. Cl.$^6$ ............................................. A61B 11/02
[52] U.S. Cl. ........................ 600/216; 600/204; 600/210; 600/215; 600/219; 600/227
[58] Field of Search ........................ 128/20; 600/226, 600/201, 204, 210, 215, 216, 219, 222, 225, 227, 228, 235, 209

[56] References Cited

U.S. PATENT DOCUMENTS

| | | |
|---|---|---|
| 658,669 | 9/1900 | Morrow . |
| 1,798,124 | 3/1931 | Hunn . |
| 2,202,748 | 5/1940 | Solo . |
| 2,313,164 | 3/1943 | Nelson . |
| 3,570,498 | 3/1971 | Weighton . |
| 4,459,978 | 7/1984 | Kotsanis . |
| 4,573,452 | 3/1986 | Greenberg . |
| 4,608,965 | 9/1986 | Anspach, Jr. et al. . |
| 5,081,983 | 1/1992 | Villalta et al. . |
| 5,152,279 | 10/1992 | Wilk . |
| 5,176,128 | 1/1993 | Andrese . |
| 5,178,133 | 1/1993 | Pena . |
| 5,183,033 | 2/1993 | Wilk . |
| 5,195,505 | 3/1993 | Josefsen . |
| 5,235,966 | 8/1993 | Jamner . |
| 5,245,987 | 9/1993 | Redmond et al. . |
| 5,318,012 | 6/1994 | Wilk . |
| 5,339,802 | 8/1994 | Cook . |
| 5,351,679 | 10/1994 | Mayzels et al. . |

FOREIGN PATENT DOCUMENTS

| | | |
|---|---|---|
| 0521088B | 3/1994 | France . |
| WO 91/14392 | 10/1991 | WIPO . |
| WO 92/18056 | 10/1992 | WIPO . |
| WO 92/21294 | 12/1992 | WIPO . |

OTHER PUBLICATIONS

Gasless Laparoscopy With Mechanical Peritoneal Distention. Origin—The Source of Laparoscopic Innovation.
A safe and simple method to maintain a clear field of vision during laparoscopic cholecystectomy, Kitano et al., Springer-Verlag New York Inc., 1992.
The Mediflex Bookler A.W.E.L. (Abdominal Wall Elevator Device) for Low Pressure Pneumoperitoneum Laparoscopic Surgery.

*Primary Examiner*—Beverly M. Flanagan
*Attorney, Agent, or Firm*—Gottlieb, Rackman & Reisman, P.C.

[57] ABSTRACT

Abdominal wall retractors is made of a plurality of extension arms to define a plane when expanded. The device is inserted through a small opening in the patient's abdomen, after which it is expanded by manipulation upon the portion remaining exterior to the patient. The retractor then elevates the abdominal wall to facilitate laparoscopic surgery, thus avoiding the need for creation of a pneumoperitoneum or the use of general anesthetic.

8 Claims, 5 Drawing Sheets

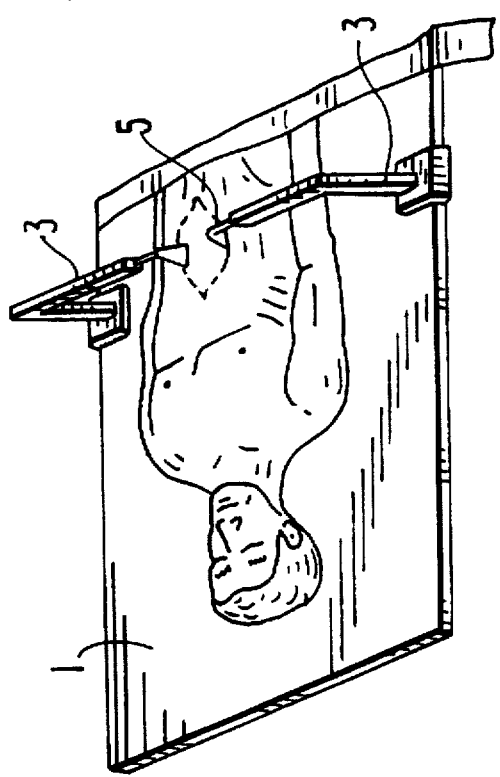
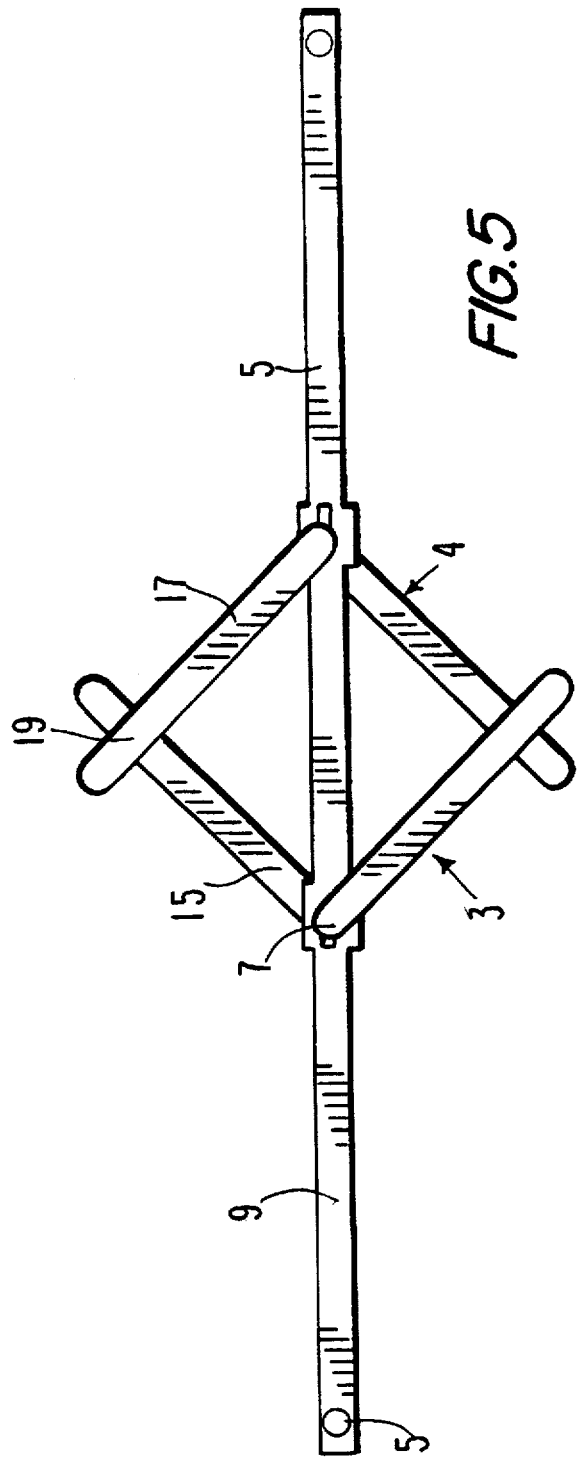

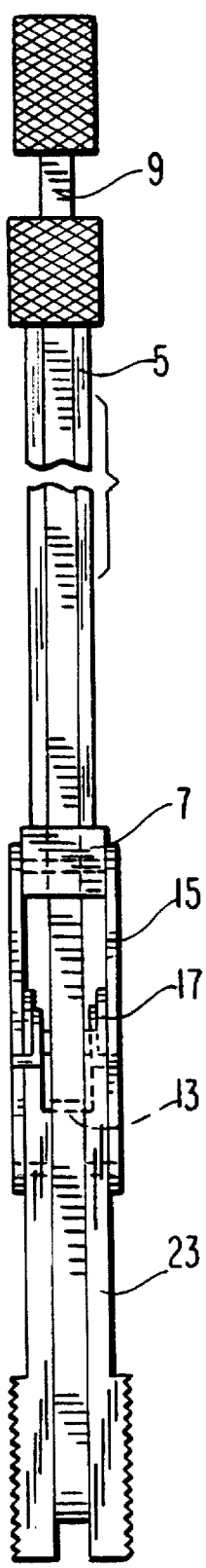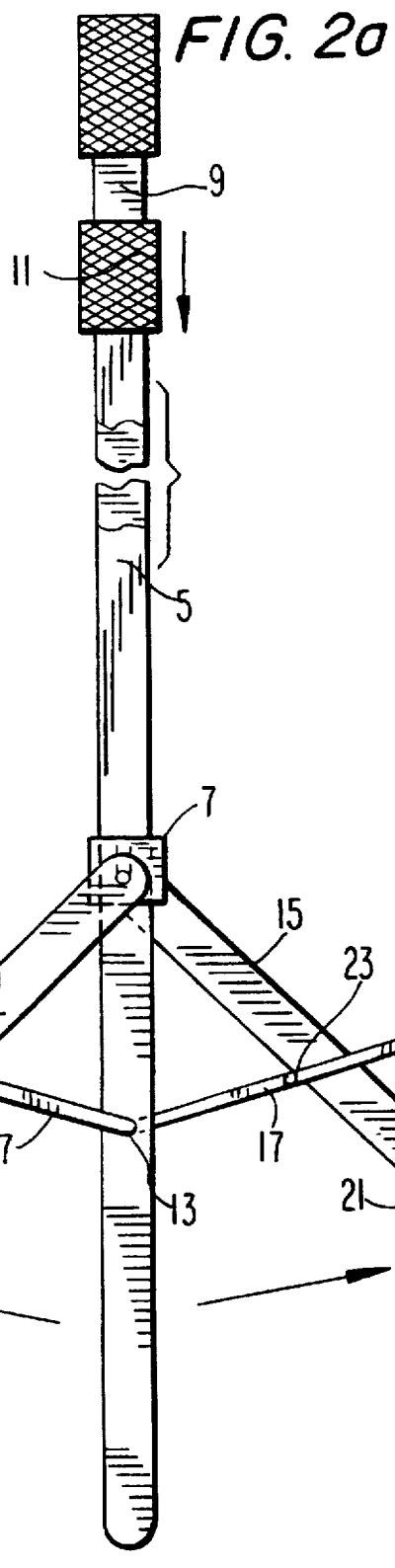
FIG. 2a
FIG. 2b

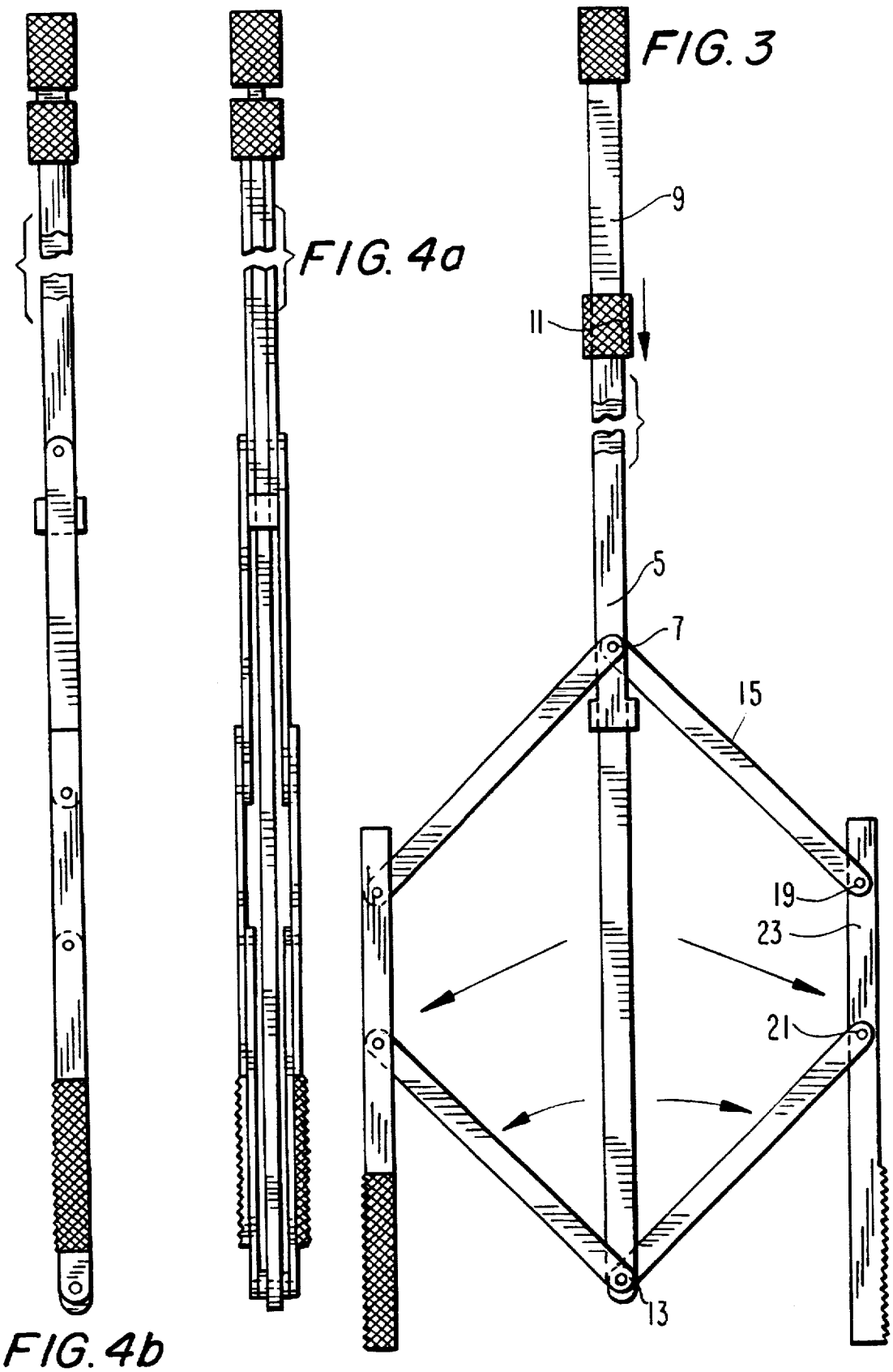

PLANAR ABDOMINAL WALL RETRACTOR FOR LAPAROSCOPIC SURGERY

This application is a continuation-in-part of application serial number 08/078,576 filed Jun. 17, 1993 now abandoned.

FIELD OF THE INVENTION

This invention relates to surgical retractors for use in conjunction with laparoscopic surgery within the abdominal cavity. In particular, it relates to an improved method for performing laparoscopic surgery employing novel planar abdominal wall retractors, without a potentially harmful and cumbersome gas induced pneumoperitoneum.

BACKGROUND OF THE INVENTION

Laparoscopic surgery involves the insertion, into a patient's abdominal cavity, through a small opening, of a surgical instrument, and a fiber optic viewing device enabling the surgeon to view the surgical field during surgery and an exploratory period prior to the surgery. In order for the viewing device (laparoscope) to function properly, it is necessary that there be a space created between the interior of the abdominal wall and the organs which are normally pressed against the abdominal wall. To create this space, it has been customary to create a pneumoperitoneum, by insufflating the peritoneal or abdominal cavity with a gas, most commonly $CO_2$, in order to elevate the abdominal wall. There are several disadvantages in this current technique. It involves the use of electronic insufflators which are costly pieces of equipment, requiring constant and careful maintenance. The $CO_2$ gas may be retained causing respiratory impairment. Furthermore, the preperitoneal insufflation of gas into the subcutaneous tissues, which is unavoidable in certain procedures, can result in a subcutaneous emphysema or pneumomediastinum (gas around the heart). Furthermore, there is the possibility of a gas embolism and the risk that during the surgery there will be loss of pneumoperitoneum when, for example, suction is utilized.

In addition, the formation of the pneumoperitoneum is an extremely painful procedure for the patient and customarily requires general anesthesia of the patient with its attendant risks.

The present invention is a method of using novel retractors in order to create a physically maintained space above the abdominal contents in order to permit viewing abdominal structures during laparoscopy, without a gas induced pneumoperitoneum.

Medical retractors are known in the prior art. For example, U.S. Pat. No. 5,081,983 to Villalta et al. issued Jan. 21, 1992 for a medical retractor device for use in abdominal surgery. The device, however, was essentially a speculum permitting examinations when a large incision has laid the abdominal wall open. The retractor of the Villalta patent is designed to enable a large opening to be held open so that the visual field inside the opening is maximized. Thus the retractor of the Villalta invention, by relying on a large opening defeats the purpose and is unsuited for use with laparoscopic surgery.

U.S. Pat. No. 5,178,133 to Pena issued Jan. 12, 1993 for a laparoscopic retractor and sheath. This retractor, however, employed a plurality of arms having a webbing between them to bear down on the contents of the intestines, rather than to lift up the abdomen. As a result, the retractor of the Pena patent facilitates a surgical procedure by retracting the internal organs. It is not designed, nor does it claim, to elevate and maintain the abdominal wall to permit gasless laparoscopy.

U.S. Pat. No. 4,459,978 to Kotsanis issued Jul. 17, 1984 for a medical retractor device. This device had fingers which spread out within a lumen of a vessel and was useful during anastomosis. It has no application to laparascopic surgery.

U.S. Pat. No. 1,798,124 to Hunn issued Mar. 24, 1931 for a urethral sound and axis traction prostatic retractor. This provided a device for mechanically opening an obstructed bladder, thus avoiding the necessity of using air for filling the bladder. The device was introduced in the closed position through the urethra and then opened slightly and withdrawn. This could be used to break up fibrous bands in the prostate and provide temporary relief from urinary obstruction. The retractor had a rod consisting of a tubular member having an end uniformly curved laterally and an enclosed rod that terminated in a second uniformly curved portion that lay concentrically against the curved end of the tubular member and capable of being turned away from the last-mentioned closed end. There were means for rotating the rod to effect the aforementioned motions of the rod. That invention has no laparoscopic application.

The Abstract entitled Nagai, H., "A New Method of Laparoscopic Cholecystectomy: An Abdominal Wall Lifting Technique Without Pneumoperitoneum", *Surgical Laparoscopy & Endoscopy*, Vol. 1, No. 2, 1991 suggests a device for raising the abdominal wall during laparoscopic surgery without a pneumoperitoneum. The device is a loop of wire placed under the abdomen and pulled upward by a winch. European Patent Office Publication 0 521 088 B1, Mar. 9, 1994 discloses a twisted wire support for maintaining an opening during laparoscopic surgery. Neither of these devices provides the wide area of support for the abdominal wall of a patient that is provided by the present invention.

In addition, the present applicant's copending application serial number 08/078,576 filed Jun. 17, 1993 disclosed a novel retractor comprising a plurality of enclosed rods having curved flats at their distal ends, which rods lay adjacent to one another until rotated and splayed out by manipulating knurled portions at their proximal ends. The splayed ends of the rod were used to support the abdominal wall of the patient. A twisting motion was required to insert the collapsed device into the abdominal cavity.

BRIEF DESCRIPTION OF THE INVENTION

The present invention resides in a method for laparoscopic surgery in the abdominal region which utilizes a novel retractor which, when inserted and engaged, holds the abdominal wall away from the abdominal contents or the viscera in order to provide a viewing region. The novel retractor is inserted straight into an incision made for the purpose. By rotating a threaded control knob, after insertion of the collapsed device, extension arms extend to define a plane and may be used to support the abdominal wall of the patient. A small incision of approximately 10 millimeters is sufficient for insertion of the device into a patient. Various embodiments of the invention are disclosed.

BRIEF DESCRIPTION OF THE DRAWINGS

FIG. 1 is a perspective view of an application of the present invention during surgery upon a patient.

FIG. 2a depicts a first embodiment the retractor of the present invention in its expanded state.

FIG. 2b depicts a side view of a first embodiment of the retractor of the present invention in its collapsed state.

FIG. 3 depicts a second embodiment of the retractor of the present invention in its expanded state.

FIG. 4a and 4b depict the second embodiment of the retractor of the present invention in its collapsed state in two orthogonal views.

FIG. 5 depicts the most preferred embodiment of the present invention in its expanded state.

DETAILED DESCRIPTION OF A PREFERRED EMBODIMENT OF THE PRESENT INVENTION

Figure 6A:
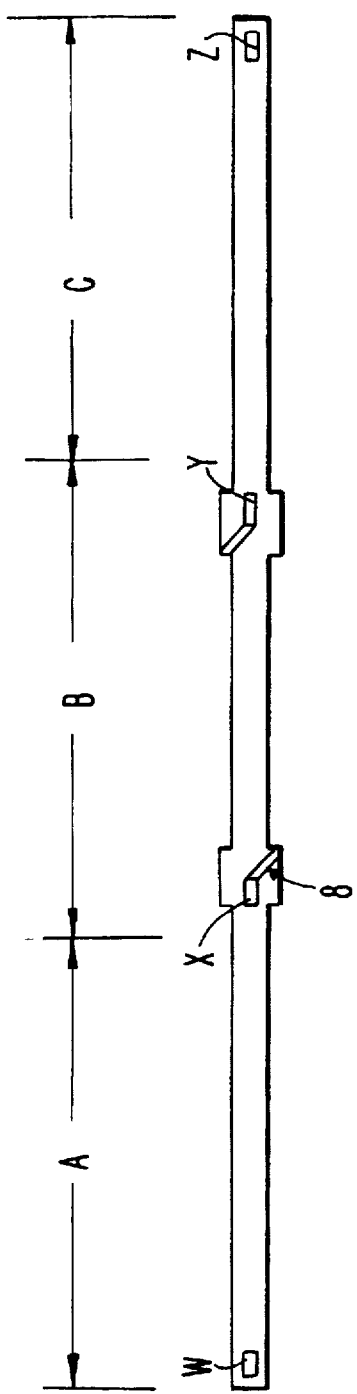
FIGS. 6a and 6b depict side and exploded views of the most preferred embodiment of the present invention.

A preferred embodiment of the present invention is a method for enabling laparoscopic surgery to proceed in a patient without the need for a gas induced pneumoperitoneum with its associated potential mechanical and clinical difficulties. In particular, it utilizes novel retractors to lift the patient's abdominal wall and create a region between the abdominal wall and the abdominal contents so that the laparoscope may be inserted to view the contents of the abdominal cavity and perform surgery upon them.

FIG. 1 depicts a patient upon an operating table 1 to which is attached, by conventional mechanical means, a rigid arm 3 which is designed to hold a retractor of the present invention. The retractor's components in one preferred embodiment are shown in FIG. 2. It comprises, in its preferred embodiment, a central rod 5 having a hinge means 7, which may be a pin extending outwardly from the axis of the rod. Internal to the rod 5, or engaged in a track along the rod 5, is a central translating rod 9, that is slidably aligned along the axis of the central rod 5. Some means 11 is provided to translate the central translating rod with respect to the central rod. It may employ threads on the central translating rod that engage a rotatable piece designated as 11 in FIG. 2, or the translating rod may simply be held in place by friction. The central translating rod has a second hinge means 13, that during translation of the rod 9 moves towards or away from the hinge means 7. First extension arms 15 have their proximal ends engaged by hinge 7. A second set of extension arms 17 are engaged by hinge 13 on central translating rod 9. The two pairs of extension arms can thus take up a collapsed position shown in FIG. 2b, in which they are aligned with the axis of the central rod, as shown in FIG. 3 and an expanded position as shown in FIG. 2A, where they define a plane. At the distal end of each of the extension arms there are further hinge means 19 and 21. In addition, one or both of the extension arms 15 and 17 may have additional hinges along their length. Intermediate extension arms 23 are hingedly connected to the previously mentioned extension arms by the hinges 19 and 21. The result is a collapsible structure, as shown in FIG. 3, which may be expanded as in FIG. 4 to a structure defining a plane by the various extension arms, said plane being capable of supporting the abdomen. In this embodiment, the retractor is designed to be supported at one end when inserted, expanded and used to elevate the patient's abdomen.

FIGS. 3 and 4 show a second embodiment in which the extension arms do not cross, but the basic design of the apparatus is similar to that of the first embodiment.

FIG. 5 shows a third and most preferred embodiment. Here the two sets of extension arms 15 and 17 are hinged to each other by hinge 19 at their proximal ends without the intercession of intermediate extension arms. Nevertheless in the expanded position a plane is defined that is utilized to elevate the abdomen of the patient. A particular advantage of this third embodiment is that it is has fewer parts and therefore can collapse into a narrower structure thereby requiring a smaller incision in the abdominal wall for its insertion. Furthermore, since it has two rods ends extending away from the defined plane, it may be supported at both ends by supporting structures as shown in FIG. 1.

The instrument is therefore designed to be inserted into the abdominal cavity in its collapsed form. Once inserted the extension arms are opened and the instrument is lifted from both sides, thus elevating the abdominal wall from the underlying viscera allowing performance of laparoscopic examination and surgery without the aid of the Carbon Dioxide gas.

Figure 6B:
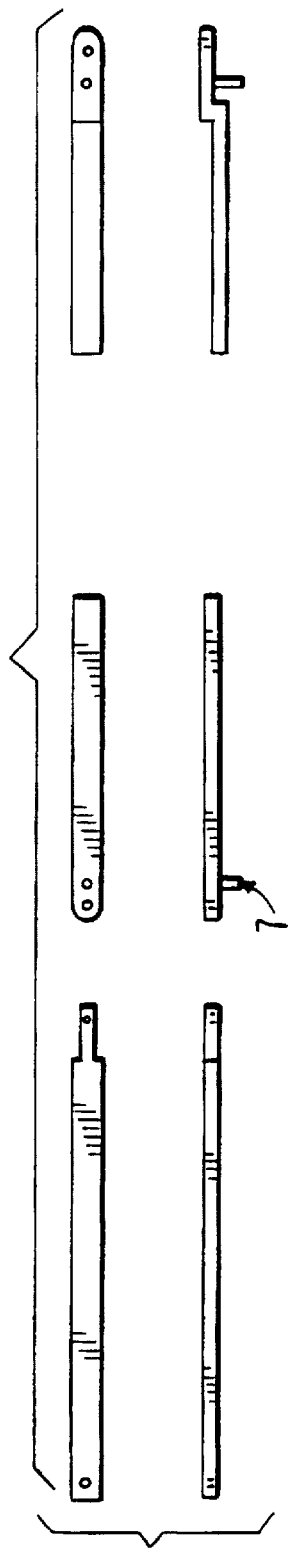
Figure 7:
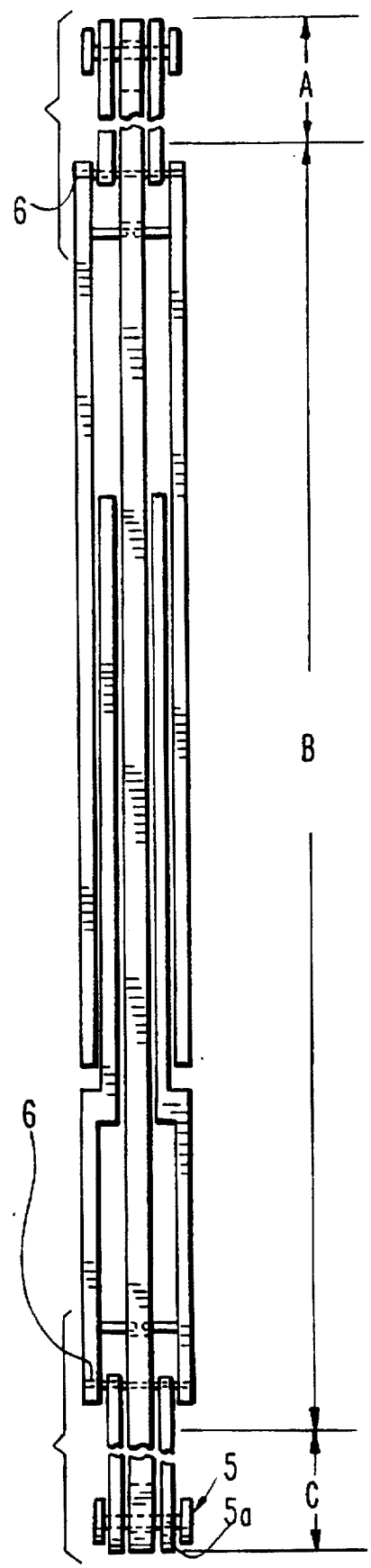
FIG. 7 depicts a view of the most preferred embodiment of the present invention in its collapsed state.

In its closed form, as shown in FIG. 6, the instrument has a rod like shape, with nothing protruding outside of the main body of the instrument, permitting easy introduction into the abdominal cavity through two small opposing stab wounds.

In a further alternative embodiment the apparatus may be constructed with a single solid central rod and the two opposing pairs of extension arms separately adjustable to positions away from the axis of the device. Then it is not necessary that they be hinged together at their distal ends. The motion of the separate pairs of extension arms may be controlled by separate threaded mechanisms on each end of the central rod. FIG. 6 depicts such an arrangement in its collapsed configuration.

Part 23 has a pin 27 on the side adjacent to part 21. The pin 27 is designed to follow tract 28. So that when the thumbscrew 25 is released and parts 22 are moved forward from closed to open position of the finger like projection the parts 23 that are attached to parts 22 by a pin 26 will move forward and angulate to 45 degrees angle from the longitudinal axis of the part 21. This will occur as the pin 27 follows the tract 28. There are altogether four tracts 28.

In the section "A" of the instrument, as it opens, the part 23 on top of part 21 will move and angulate to the right simultaneously as part 23 on the bottom of part 21 will move and angulate to the left. Both parts 23 when fully angulated will form a 45 degrees angle with the main body of the instrument.

Mechanism of section "C" is analogous to that of section "A" with the exception of a downward step in section 24 that will permit it to be located in between parts 21 and 23 when the instrument is closed.

The apparatus measures about 10 millimeters in outside diameter in its collapsed configuration, having the length of about 120 centimeters. Each of the flat extension arms is approximately 2 millimeters in thickness, 10 millimeters in width and 20 centimeters in length in the most preferred embodiment. An incision having the length of approximately 10 millimeters is made in the abdomen of the patient. The retractor is inserted and worked through the incision. Once inserted within the patient, the extension arms are spread out, for example, making equal angles with respect to the rod axis of approximately 45°. The device is then lifted to raise the wall of the abdominal cavity and to create a space between the inner wall of the abdominal cavity and the abdominal contents. A laparoscopic device may then be inserted through a second incision made in the patient and whatever surgical procedure is being done laparoscopically may then be performed. In this manner, the invention is performed without the necessity of injecting gases such as carbon monoxide to create a suitable pneumoperitoneum.

The rods and extension arms will maintain their open configuration in the abdominal cavity by virtue of counterpressure against them provided by the abdominal wall itself.

Upon completion of the laparoscopic surgery, the apparatus may be collapsed to facilitate removal of the device from the patient.

Although the preferred embodiments of the invention has been described in some detail, the invention is not limited to the details of this preferred embodiment, but is instead described by the subject matter of the following claims.

I claim:

1. A retractor for elevating the abdominal wall of a patient with respect to an operating table during abdominal laparoscopic surgery comprising:

a central rod having
first proximal hinge means,
a central translating rod slidably aligned along the axis of said central rod and having thereon
means to translate said central translating rod along the axis of said central rod, said central translating rod further comprising
second proximal hinge means, said first and second proximal hinge means being means for hingedly engaging
respective first and second extension arms at a proximal end thereof, wherein said first and second extension arms are pivotable about said respective first and second proximal hinge means from a position aligned along said central rod to a position extending outwardly from said central rod, said first and second extension arms each having
distal hinge means at a distance from said corresponding proximal hinge means to hingedly connect said corresponding extension arm to an intermediate extension arm,
wherein translation of said central translating rod moves said first proximal hinge means with respect to said second proximal hinge means and therein causes said extension arms to move from a closed position aligned along said central rod, in which closed position said central rod may be inserted into a small opening made in the abdominal wall of a patient, to an open position lying in a lifting plane parallel to a plane containing the axis of said central rod, in which open position said extension arms comprise means to lift an abdominal wall,
further comprising support means for elevating said central rod above said operating table, wherein the abdominal wall of the patient is elevated with respect to the operating table.

2. The retractor of claim 1 wherein said extension arms are respectively each one of a pair of extension arms symmetrically located on opposite sides of the axis of the central rod.

3. The retractor of claim 1 wherein said means to translate comprises rotatable threaded means and said central translating rod is threaded to engage said rotatable threaded means, wherein rotation of said rotatable threaded means causes translation of said central translating rod.

4. The retractor of claim 1 wherein said first and second extension arms have the same length between their respective proximal and distal hinge means, and said intermediate extension arm is parallel to the axis of said central rod in both the open and closed position.

5. A retractor for elevating the abdominal wall of a patient with respect to an operating table during abdominal laparoscopic surgery comprising:

a central rod having
first proximal hinge means,
a central translating rod slidably aligned along the axis of said central rod and having thereon
means to translate said central translating rod along the axis of said central rod, said central translating rod further comprising
second proximal hinge means, said first and second proximal hinge means being means for hingedly engaging
respective first and second extension arms at a proximal end thereof, wherein said first and second extension arms are pivotable about said respective first and second proximal hinge means from a position aligned along said central rod to a position extending outwardly from said central rod, said first and second extension arms each having
distal hinge means at a distance from said corresponding proximal hinge means to hingedly connect said corresponding extension arm to an intermediate extension arm,
wherein translation of said central translating rod moves said first proximal hinge means with respect to said second proximal hinge means and therein causes said extension arms to move from a closed position aligned along said central rod, in which closed position said central rod may be inserted into a small opening made in the abdominal wall of a patient, to an open position lying in a lifting plane parallel to a plane containing the axis of said central rod, in which open position said extension arms comprise means to lift an abdominal wall,
wherein said hinges are arranged so that motion of said first and second hinge means closer together causes said first and second extension arms to move outward from the axis of said central rod.

6. A retractor for elevating the abdominal wall of a patient with respect to an operating table during abdominal laparoscopic surgery comprising:

a central rod having
first proximal hinge means,
a central translating rod slidably aligned along the axis of said central rod and having thereon
means to translate said central translating rod along the axis of said central rod, said central translating rod further comprising
second proximal hinge means, said first and second proximal hinge means being means for hingedly engaging
respective first and second extension arms at a proximal end thereof, wherein said first and second extension arms are pivotable about said respective first and second proximal hinge means from a position aligned along said central rod to a position extending outwardly from said central rod, said first and second extension arms each having
distal hinge means at a distance from said corresponding proximal hinge means to hingedly connect said corresponding extension arm to an intermediate extension arm,
wherein translation of said central translating rod moves said first proximal hinge means with respect to said second proximal hinge means and therein causes said extension arms to move from a closed position aligned along said central rod, in which closed position said central rod may be inserted into a small opening made in the abdominal wall of a patient, to an open position lying in a lifting plane parallel to a plane containing the axis of said central rod, in which open position said extension arms comprise means to lift an abdominal wall,
wherein said hinges are arranged so that motion of said first and second hinge means further apart from each other causes said first and second extension arms to move closer to the axis of said central rod.

7. A method for elevating the abdominal wall of a patient during abdominal laparoscopic surgery comprising surgically forming one or more openings in said wall, inserting intra-abdominally through said opening(s) a portion of a retractor comprising a central rod having first proximal hinge means, a central translating rod slidably aligned along the axis of said central rod and having thereon means to translate said central translating rod along the axis of said central rod, said central translating rod further comprising second proximal hinge means, said first and second proximal hinge means being means for hingedly engaging respective first and second extension arms at a proximal end thereof, wherein said first and second extension arms are pivotable about said respective first and second proximal hinge means from a position aligned along said central rod to a position extending outwardly from said central rod, said first and second extension arms each having distal hinge means at a distance from said corresponding proximal hinge means to hingedly connect said corresponding extension arm to an intermediate extension arm, translating said central translating rod to move said first proximal hinge means with respect to said second proximal hinge means and thereby causing said extension arms to move from a closed position aligned along said central rod to an open position lying in a lifting plane parallel to a plane containing the axis of said central rod, in which open position said extension arms comprise means to lift an abdominal wall, elevating the patient's abdominal wall to create an inter-abdominal space by lifting said retractor against the patient's abdominal wall, performing laparoscopic surgery in the interabdominal cavity formed between said abdominal wall and said patient's abdominal contents, wherein the retractor maintains constant exposure of the abdominal contents regardless of suction within the inter-abdominal space.

8. The method of claim 7 further comprising attaching said retractor to support means for elevating said central rod above said operating table, wherein the abdominal wall of the patient is elevated with respect to the operating table.

* * * * *